United States Patent [19]

Burk et al.

[11] Patent Number: 5,710,288

[45] Date of Patent: Jan. 20, 1998

[54] 1,3-BENZODIOXOLE AND 1,2-DIALKOXYBENZENE DERIVATIVES AS OCULAR HYPOTENSIVE AGENTS

[75] Inventors: Robert M. Burk, Laguna Beach; David F. Woodward, El Toro, both of Calif.

[73] Assignee: Allergan, Waco, Tex.

[21] Appl. No.: 646,697

[22] Filed: May 3, 1996

Related U.S. Application Data

[63] Continuation-in-part of Ser. No. 345,176, Nov. 28, 1994, Pat. No. 5,523,296, which is a continuation-in-part of Ser. No. 51,104, Apr. 21, 1993, Pat. No. 5,369,127.

[51] Int. Cl.$^6$ .................... C07D 409/10; C07D 407/10
[52] U.S. Cl. .................... 549/435; 549/5; 549/6; 549/60; 549/220; 549/362; 548/112; 548/202; 548/203; 548/204; 548/205; 548/214; 548/235; 548/236; 548/247; 548/336; 546/22; 546/270; 544/232; 544/238; 544/243; 544/333; 544/337; 544/405
[58] Field of Search ................ 549/5, 6, 60, 220, 549/362, 435; 548/112, 202, 203, 204, 205, 214, 235, 236, 247, 336; 546/22, 270; 544/232, 238, 243, 333, 337, 405

[56] References Cited

PUBLICATIONS

Basseiso et al., J. Chem. Res. Synop. (7), 220–221 (1985).

*Primary Examiner*—Nicky Chan
*Attorney, Agent, or Firm*—Gabor L. Szekeres; Robert J. Baran; Martin A. Voet

[57] ABSTRACT

Compounds of the formula

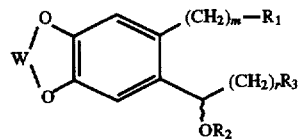

where the symbols have the meaning defined in the specification, are capable of lowering intraocular pressure in the eye of a mammal.

15 Claims, No Drawings

1,3-BENZODIOXOLE AND 1,2-DIALKOXYBENZENE DERIVATIVES AS OCULAR HYPOTENSIVE AGENTS

CROSS-REFERENCE TO RELATED APPLICATION

The present application is a continuation-in-part of application Ser. No. 08/345,176 filed on Nov. 28, 1994 now U.S. Pat. No. 5,523,296, which is a continuation-in-part of application Ser. No. 08/051,104, filed Apr. 21, 1993, now U.S. Pat. No. 5,369,127.

FIELD OF THE INVENTION

The present invention relates to novel 1,2-benzodioxole and 1,2-dialkoxybenzene derivatives substituted in the aromatic portion with a 1-hydroxy-(heteroaryl)-alkyl group which is itself substituted in the heteroaryl portion. The compounds are active as ocular hypotensive agents. The present invention also relates to methods of administering a pharmaceutical composition containing one or more of said 1,2-benzodioxole and 1,2-dialkoxybenzene derivatives to a mammal for the purpose of lowering the intraocular pressure in the eye of the mammal.

BACKGROUND OF THE INVENTION

Ocular hypotensive agents are useful in the treatment of a number of various ocular hypertensive conditions, such as post-surgical and post-laser trabeculectomy ocular hypertensive episodes, glaucoma, and as presurgical adjuncts.

Glaucoma is a disease of the eye characterized by increased intraocular pressure. On the basis of its etiology, glaucoma has been classified as primary or secondary. For example, primary glaucoma in adults (congenital glaucoma) may be either open-angle or acute or chronic angle-closure. Secondary glaucoma results from pre-existing ocular diseases such as uveitis, intraocular tumor or an enlarged cataract.

The underlying causes of primary glaucoma are not yet known. The increased intraocular tension is due to the obstruction of aqueous humor outflow. In chronic open-angle glaucoma, the anterior chamber and its anatomic structures appear normal, but drainage of the aqueous humor is impeded. In acute or chronic angle-closure glaucoma, the anterior chamber is shallow, the filtration angle is narrowed, and the iris may obstruct the trabecular meshwork at the entrance of the canal of Schlemm. Dilation of the pupil may push the root of the iris forward against the angle, and may produce pupillary block and thus precipitate an acute attack. Eyes with narrow anterior chamber angles are predisposed to acute angle-closure glaucoma attacks of various degrees of severity.

Secondary glaucoma is caused by any interference with the flow of aqueous humor from the posterior chamber into the anterior chamber and subsequently, into the canal of Schlemm. Inflammatory disease of the anterior segment may prevent aqueous escape by causing complete posterior synechia in iris bombe and may plug the drainage channel with exudates. Other common causes are intraocular tumors, enlarged cataracts, central retinal vein occlusion, trauma to the eye, operative procedures and intraocular hemorrhage.

Considering all types together, glaucoma occurs in about 2% of all persons over the age of 40 and may be asymptotic for years before progressing to rapid loss of vision. In cases where surgery is not indicated, topical B-adrenoreceptor antagonists have traditionally been the drugs of choice for treating glaucoma.

Prostaglandins were earlier regarded as potent ocular hypertensives; however, evidence accumulated in the last two decades shows that some prostaglandins are highly effective ocular hypotensive agents and are suitable for the long-term medical management of glaucoma. (See, for example, M. S. Starr, Exp. Eye Res. 11, 170–177, (1971); Bito, L. Z. Biological Protection with Prostaglandisn Cohen, M. M., ed., Boca Raton, Fla. CRC Press Inc., 1985, pp. 231–252; and Bito, L. Z., Applied Pharmacology in the Medical Treatment of Glaucomas Drance, S. M. and Neufeld, A. H. eds., New York, Grune & Stratton, 1984, pp. 477–505). There are numerous patent and other disclosures in the prior art describing prostaglandins as ocular hypotensive agents.

In addition to prostaglandins, several other types of chemical compounds are disclosed in the patent and scientific literature as ocular hypotensive agents. For example U.S. Pat. Nos. 5,066,644, 5,091,528, 5,151,440 assigned to the same assignee as the present application, disclose certain oxazoline, thiazoline, imidazoline and 1,4-benzoxazine derivatives as ocular hypotensive agents. An article in Journal of Medicinal Chemistry 1975, Vol. 18, pp 1094–1098 by Bender et al., describe certain heterocyclic homoprostanoids. These compounds, however, are not described to have ocular hypotensive properties.

In J. Chem. Research(s) 1985, 220–221 Barreiro et al. describe the synthesis of 5-[6-(1-hydroxyhexyl)-1,3-benzodioxol-5-yl]-acetic and pentanoic acids as potential anti-inflammatory agents.

U.S. Pat. No. 5,369,127, assigned to the same assignee as the present application, discloses 1,2-benzodioxole and 1,2-dialkoxybenzene derivatives containing 1-hydroxy-alkyl, 1-hydroxy-(phenyl)-alkyl and 1-hydroxy-(heteroaryl)-alkyl groups as a substituent in the aromatic ring of the 1,2-benzodioxole or 1,2-dialkoxybenzene nucleus. The presently known ocular hypotensive agents, however, do not cure or alleviate glaucoma and ocular hypertension in a fully satisfactory manner, and/or without undesirable side effects. For this reason, the search continues in the art for further ocular hypotensive agents, particularly for agents which are more effective, have lesser side-effects or act through a different biological mechanism than presently known ocular hypotensives.

SUMMARY OF THE INVENTION

Novel compounds of the present invention are shown by Formula 1

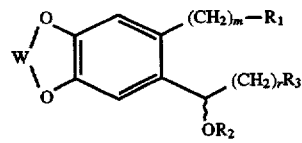

Formula 1 where

W is $(CH_2)_n$ where n is 1 or 2, or n is 0 and W represents lower alkyl groups attached to each oxygen;

m is an integer between 1 and 8;

$R_1$ is COOH or a pharmaceutically acceptable salt thereof, $COOR_4$, $CONR_5R_6$, $CONR_5SO_2R$, $CH_2OH$, $CH_2OR_7$, $CH_2O-COR_7$, $CH_2OCONR_5R_7$, $CH_2OCOOR_7$, $CH_2NH_2$, $CH_2NR_5R_6$, $CH_2NR_5COR_7$, CHO, $CH(OR_8)_2$, $CHOR_9O$, $-COR_{10}$, $CR_{10}(OR_8)_2$, or $CR_{10}OR_9O$, where $R_4$ is an alkyl group of 1 to 10 carbons, or a cycloalkyl group of 5 to 10 carbons, or $R_4$ is phenyl or lower alkyl phenyl, $R_5$ and $R_6$ independently are hydrogen, an alkyl group of 1 to 10 carbons, or a cycloalkyl group of 5 to 10 carbons, or phenyl or lower alkylphenyl, $R_7$ is alkyl of 1 to 10 carbons, phenyl or lower alkylphenyl, $R_8$ is lower alkyl, and $R_9$ is divalent alkyl radical of 2–5 carbons, $R_{10}$ is an alkyl or cycloalkcyl containing 1 to 5 carbons;

$R_2$ is H, $COR_7$, $R_7$, $CO-OR_7$, $CO-NR_5R_7$, $PO(OH)OR_7$, $PO(OR_7)_2$, $POR_7OH$, or $POR_7(OR_7)$;

$R_3$ is HETEROCYCLIC-$(R_{11})_p$, where HETEROCYCLIC is a 5 or six-membered heterocyclic ring containing 1 or 2 heteroatoms selected from N, S, and O;

$R_{11}$ is H, lower alkyl of 1–6 carbons, halogen, fluoro-substituted lower alkyl of 1–6 carbons, $C\equiv N$, $NO_2$, $SO_2R_{12}$, COOH, $COOR_{12}$, $CONH_2$, $CONHR_{12}$, $CON(R_{12})_2$, or $CO-R_{12}$;

p is an integer between 1–3, r is an integer between 1–5, and $R_{12}$ is lower alkyl of 1–6 carbons.

In another aspect the present invention relates to pharmaceutical compositions containing as active ingredient one or more compounds of the present invention (or their pharmaceutically acceptable salts).

In still another aspect the present invention relates to methods of administering to a mammal a pharmaceutical composition having as its active ingredient one or more compounds of Formula 1 (or theft pharmaceutically acceptable salts) for the purpose of lowering intraocular pressure in the eye of the mammal.

DETAILED DESCRIPTION OF THE INVENTION GENERAL EMBODIMENTS

The present invention relates to novel compounds of Formula 1, and to theft use in pharmaceutical compositions and methods for the purpose of lowering intraocular pressure in the eye of a mammal.

Definitions

The term alkyl refers to and covers any and all groups which are known as normal alkyl, branch-chain alkyl and cycloalkyl. Lower alkyl means the above-defined broad definition of alkyl groups having 1 to 6 carbons, and as applicable, 3 to 6 carbons for branch chained and cyclo-alkyl groups.

The term "ester" as used here refers to and covers any compound falling within the definition of that term classically used in organic chemistry. Where the ester is derived from a carboxylic acid corresponding to Formula 1, the term covers the products derived from the treatment of this function with alcohols, preferably with aliphatic alcohols having 1–6 carbons. Where the ester is derived from alcohols corresponding to Formula 1, the term covers compounds of the formula —$CH_2OCOR_7$ where $R_7$ is defined as in connection with Formula 1.

Amide has the meaning classically accorded that term in organic chemistry. In this instance it includes but is not limited to unsubstituted amides and aliphatic mono-and di-substituted amides.

A pharmaceutically acceptable salt may be prepared for any compound used in the method of treatment of this invention, if the compound has a functionality capable of forming such salt, for example an acid functionality. A pharmaceutically acceptable salt may be any salt which retains the activity of the parent compound and does not impart any deleterious or untoward effect on the subject to which it is administered and in the context in which it is administered.

Such a salt may be derived from any organic or inorganic acid or base. The salt may be a mono or polyvalent ion. Of particular interest where the acid function is concerned are the inorganic ions, sodium, potassium, calcium, and magnesium. Organic amine salts may be made with amines, particularly ammonium salts such as mono-, di- and trialkyl amines or ethanol amines. Salts may also be formed with caffeine, tromethanine and similar molecules. Where there is a nitrogen sufficiently basic as to be capable of forming acid addition salts, such may be formed with any inorganic or organic acids or alkylating agent such as methyl iodide. Preferred salts are those formed with inorganic acids such as hydrochloric acid, sulfuric acid or phosphoric acid. Any of a number of simple organic acids such as mono-, di- or tri-acid may also be used.

The compounds of the present invention contain one or more chiral centers and therefore exist in enantiomeric and in the event of two or more chiral esters exist in diastereomeric forms. Unless the structural formula or the language of this application specifically designate a particular configuration of a chiral center, the scope of the present invention is intended to cover all such isomers per se, as well as mixtures of diastereomers and racemic mixtures of enantiomers (optical isomers) as well.

General Description of the Preferred Compounds of the Invention

Referring now to the structure shown in Formula 1, compounds are preferred in accordance with the present invention where the symbol W represents normal-lower alkyl groups attached to each oxygen of the benzene ring, or where W represents $(CH_2)_n$ and n is 1.

With regard to the symbol m, compounds are preferred where m is between 3 to 5, and even more preferred where m is 4. For the integer r, compounds are preferred where r is 2.

Regarding $R_1$, compounds are preferred in accordance with the present invention where $R_1$ is COOH, $CH_2OH$ or $COOR_4$ where $R_4$ is lower alkyl, particularly methyl.

With regard to the group $R_2$, compounds are preferred in accordance with the present invention where $R_2$ is H, or $COR_7$ where $R_7$ is lower alkyl, particularly methyl.

With regard to the $R_3$ group, compounds are preferred where the HETEROCYCLIC group of $R_3$ is a divalent radical of furan, thiophene, thiazole, isothiazole, oxazole, isoxazole, imidazole, pyrridazole, pyridine, pyrimidine, pyrazine or pyridazine. Even more preferred for the HETEROCYCLIC group are divalent radicals of furan, thiophene, thiazole and oxazole. Moreover, for the $R_{11}$ substituent of the HETEROCYCLIC group the following are preferred: lower alkyl, halogen, $CF_3$ and other fluoro-substituted lower alkyl, $NO_2$, and $SO_2R_{12}$ especially where $R_{12}$ is methyl. The most preferred substituents of the HETEROCYCLIC group are lower alkyl, halogen and $CF_3$.

Particularly preferred are compounds where $R_3$ is 2-thienylethyl, 2-furylethyl, 4-thienylethyl, 4-furylethyl and methyl, halogen or trifluoromethyl substituted 2-thienylethyl, 2-furylethyl, 4-thienylethyl, 4-furylethyl groups where the methyl, halogen or trifluoromethyl substituents are in the 5 or 2 positions of the heterocycle, respectively.

The general structures of the most preferred compounds of the invention are shown by the structures of Formula 2 and Formula 3 below.

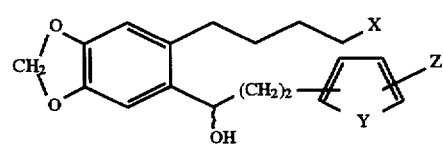

Formula 2

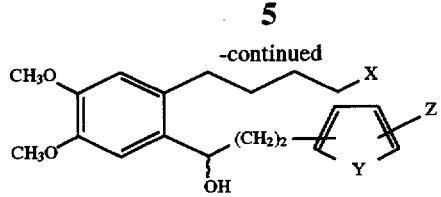

-continued

Formula 3 where X is COOCH$_3$, COOH, or CH$_2$OH;

Y is S or O;

Z is lower alkyl of 1-6 carbons, halogen or CF$_3$.

Specific examples of preferred compounds are provided in Table 1 below, which still refers to Formula 2 and Formula 3.

TABLE 1

| Compound No. | Formula | X | Y | Z | Position of Hydroxy-ethylene Group | Position of Z Group |
|---|---|---|---|---|---|---|
| 1 | 2 | CO$_2$CH$_3$ | O | CH$_3$ | 2 | 5 |
| 2 | 2 | CO$_2$CH$_3$ | O | Br | 2 | 5 |
| 3 | 2 | CO$_2$CH$_3$ | O | CF$_3$ | 2 | 5 |
| 4 | 2 | CO$_2$CH$_3$ | S | CH$_3$ | 2 | 5 |
| 5 | 2 | CO$_2$CH$_3$ | S | Br | 2 | 5 |
| 6 | 2 | CO$_2$CH$_3$ | S | CF$_3$ | 2 | 5 |
| 7 | 2 | CH$_2$OH | O | CH$_3$ | 2 | 5 |
| 8 | 2 | CH$_2$OH | O | Br | 2 | 5 |
| 9 | 2 | CH$_2$OH | O | CF$_3$ | 2 | 5 |
| 10 | 2 | CH$_2$OH | S | CH$_3$ | 2 | 5 |
| 11 | 2 | CH$_2$OH | S | Br | 2 | 5 |
| 12 | 2 | CH$_2$OH | S | CF$_3$ | 2 | 5 |
| 13 | 2 | CO$_2$H | O | CH$_3$ | 2 | 5 |
| 14 | 2 | CO$_2$H | O | Br | 2 | 5 |
| 15 | 2 | CO$_2$H | O | CF$_3$ | 2 | 5 |
| 16 | 2 | CO$_2$H | S | CH$_3$ | 2 | 5 |
| 17 | 2 | CO$_2$H | S | Br | 2 | 5 |
| 18 | 2 | CO$_2$H | S | CF$_3$ | 2 | 5 |
| 19 | 3 | CO$_2$H | O | CH$_3$ | 2 | 5 |
| 20 | 3 | CO$_2$H | O | Br | 2 | 5 |
| 21 | 3 | CO$_2$H | O | CF$_3$ | 2 | 5 |
| 22 | 3 | CO$_2$H | S | CH$_3$ | 2 | 5 |
| 23 | 3 | CO$_2$H | S | Br | 2 | 5 |
| 24 | 3 | CO$_2$H | S | CF$_3$ | 2 | 5 |
| 25 | 3 | CO$_2$CH$_3$ | O | CH$_3$ | 2 | 5 |
| 26 | 3 | CO$_2$CH$_3$ | O | Br | 2 | 5 |
| 27 | 3 | CO$_2$CH$_3$ | O | CF$_3$ | 2 | 5 |
| 28 | 3 | CO$_2$CH$_3$ | S | CH$_3$ | 2 | 5 |
| 29 | 3 | CO$_2$CH$_3$ | S | Br | 2 | 5 |
| 30 | 3 | CO$_2$CH$_3$ | S | CF$_3$ | 2 | 5 |
| 31 | 3 | CH$_2$OH | O | CH$_3$ | 2 | 5 |
| 32 | 3 | CH$_2$OH | O | Br | 2 | 5 |
| 33 | 3 | CH$_2$OH | O | CF$_3$ | 2 | 5 |
| 34 | 3 | CH$_2$OH | S | CH$_3$ | 2 | 5 |
| 35 | 3 | CH$_2$OH | S | Br | 2 | 5 |
| 36 | 3 | CH$_2$OH | S | CF$_3$ | 2 | 5 |
| 37 | 2 | CO$_2$CH$_3$ | O | CH$_3$ | 4 | 2 |
| 38 | 2 | CO$_2$CH$_3$ | O | Br | 4 | 2 |
| 39 | 2 | CO$_2$CH$_3$ | O | CF$_3$ | 4 | 2 |
| 40 | 2 | CO$_2$CH$_3$ | S | CH$_3$ | 4 | 2 |
| 41 | 2 | CO$_2$CH$_3$ | S | Br | 4 | 2 |
| 42 | 2 | CO$_2$CH$_3$ | S | CF$_3$ | 4 | 2 |
| 43 | 2 | CH$_2$OH | O | CH$_3$ | 4 | 2 |
| 44 | 2 | CH$_2$OH | O | Br | 4 | 2 |
| 45 | 2 | CH$_2$OH | O | CF$_3$ | 4 | 2 |
| 46 | 2 | CH$_2$OH | S | CH$_3$ | 4 | 2 |
| 47 | 2 | CH$_2$OH | S | Br | 4 | 2 |
| 48 | 2 | CH$_2$OH | S | CF$_3$ | 4 | 2 |
| 49 | 2 | CO$_2$H | O | CH$_3$ | 4 | 2 |
| 50 | 2 | CO$_2$H | O | Br | 4 | 2 |
| 51 | 2 | CO$_2$H | O | CF$_3$ | 4 | 2 |
| 52 | 2 | CO$_2$H | S | CH$_3$ | 4 | 2 |
| 53 | 2 | CO$_2$H | S | Br | 4 | 2 |
| 54 | 2 | CO$_2$H | S | CF$_3$ | 4 | 2 |
| 55 | 3 | CO$_2$H | O | CH$_3$ | 4 | 2 |
| 56 | 3 | CO$_2$H | O | Br | 4 | 2 |
| 57 | 3 | CO$_2$H | O | CF$_3$ | 4 | 2 |
| 58 | 3 | CO$_2$H | S | CH$_3$ | 4 | 2 |
| 59 | 3 | CO$_2$H | S | Br | 4 | 2 |
| 60 | 3 | CO$_2$H | S | CF$_3$ | 4 | 2 |
| 61 | 3 | CO$_2$CH$_3$ | O | CH$_3$ | 4 | 2 |
| 62 | 3 | CO$_2$CH$_3$ | O | Br | 4 | 2 |
| 63 | 3 | CO$_2$CH$_3$ | O | CF$_3$ | 4 | 2 |
| 64 | 3 | CO$_2$CH$_3$ | S | CH$_3$ | 4 | 2 |
| 65 | 3 | CO$_2$CH$_3$ | S | Br | 4 | 2 |
| 66 | 3 | CO$_2$CH$_3$ | S | CF$_3$ | 4 | 2 |
| 67 | 3 | CH$_2$OH | O | CH$_3$ | 4 | 2 |
| 68 | 3 | CH$_2$OH | O | Br | 4 | 2 |
| 69 | 3 | CH$_2$OH | O | CF$_3$ | 4 | 2 |
| 70 | 3 | CH$_2$OH | S | CH$_3$ | 4 | 2 |
| 71 | 3 | CH$_2$OH | S | Br | 4 | 2 |
| 72 | 3 | CH$_2$OH | S | CF$_3$ | 2 | 2 |
| 73 | 2 | CO$_2$CH$_3$ | S | H | 2 | 5 |
| 74 | 2 | CH$_2$OH | S | H | 2 | 5 |
| 75 | 2 | COOH | S | H | 2 | 5 |

Methods of Administration, Formulations

Pharmaceutical compositions may be prepared by combining a therapeutically effective amount of at least one compound according to the present invention, or a pharmaceutically acceptable salt thereof, as an active ingredient, with conventional ophthalmically acceptable pharmaceutical excipients, and by preparation of unit dosage forms suitable for topical ocular use. The therapeutically efficient amount typically is between about 0.0001 and about 5% (w/v), preferably about 0.001 to about 1.0% (w/v) in liquid formulations.

For ophthalmic application, preferably solutions are prepared using a physiological saline solution as a major vehicle. The pH of such ophthalmic solutions should preferably be maintained between 4.5 and 8.0 with an appropriate buffer system, a neutral pH being preferred but not essential. The formulations may also contain conventional, pharmaceutically acceptable preservatives, stabilizers and surfactants.

Preferred preservatives that may be used in the pharmaceutical compositions of the present invention include, but are not limited to, benzalkonium chloride, chlorobutanol, thimerosal, phenylmercuric acetate and phenylmercuric nitrate. A preferred surfactant is, for example, Tween 80. Likewise, various preferred vehicles may be used in the ophthalmic preparations of the present invention. These vehicles include, but are not limited to, polyvinyl alcohol, povidone, hydroxypropyl methyl cellulose, poloxamers, carboxymethyl cellulose, hydroxyethyl cellulose cyclodextrin and purified water.

Tonicity adjustors may be added as needed or convenient. They include, but are not limited to, salts, particularly sodium chloride, potassium chloride, mannitol and glycerin, or any other suitable ophthalmically acceptable tonicity adjustor.

Various buffers and means for adjusting pH may be used so long as the resulting preparation is ophthalmically acceptable. Accordingly, buffers include acetate buffers, citrate buffers, phosphate buffers and borate buffers. Acids or bases may be used to adjust the pH of these formulations as needed.

In a similar vein, an ophthalmically acceptable antioxidant for use in the present invention includes, but is not limited to, sodium metabisulfite, sodium thiosulfate, acetylcysteine, butylated hydroxyanisol and butylated hydroxytoluene.

Other excipient components which may be included in the ophthalmic preparations are chelating agents. The preferred chelating agent is edentate disodium, although other chelating agents may also be used in place or in conjunction with it.

The ingredients are usually used in the following amounts:

| Ingredient | Amount (% w/v) |
| --- | --- |
| active ingredient | about 0.001–5 |
| preservative | 0–0.10 |
| vehicle | 0–40 |
| tonicity adjustor | 0–10 |
| buffer | 0.01–10 |
| pH adjustor | q.s. pH 4.5–7.5 |
| antioxidant | as needed |
| surfactant | as needed |
| purified water | as needed to make 100% |

The actual dose of the active compounds of the present invention depends on the specific compound, and on the condition to be treated; the selection of the appropriate dose is well within the knowledge of the skilled artisan.

The ophthalmic formulations of the present invention are conveniently packaged in forms suitable for metered application, such as in containers equipped with a dropper, to facilitate application to the eye. Containers suitable for dropwise application are usually made of suitable inert, non-toxic plastic material, and generally contain between about 0.5 and about 15 ml solution. One package may contain one or more unit doses.

Especially preservative-free solutions are often formulated in non-resealable containers containing up to about ten, preferably up to about five units doses, where a typical unit dose is from one to about 8 drops, preferably one to about 3 drops. The volume of one drop is about 20–35 µl.

Biological Activity.

The ability of a pharmaceutical composition which contains a compound of Formula 1 to lower intraocular pressure in the eye of a mammal, can be demonstrated by an assay performed on the eyes of dogs. The assay is described as follows: male and female beagle dogs weighing 10–15 kg are trained for a minimum of 2 months so that intraocular pressure can be measured without the use of restraining devices. Intraocular pressure is measured by pneumatonometry using applanation tonometers (Alcon). One minute prior to tonometry, 25 µl of proparacaine (Allergan, Irvine Calif.) is applied to minimize ocular discomfort during the procedure. Determination of the effects of the compounds of the invention on intraocular pressure involve administration of 1 to 25 µl of solution of the compound to one eye and an equal volume of vehicle to the contralateral eye as a control.

Other assays well known in the art for determining the intraocular pressure (IOP) lowering effect of compounds can also be used to measure the effect of the compounds of the invention on IOP in experimental animals, such as rabbits or monkeys.

The ability of compounds of the invention to inhibit DNA synthesis can be determined in an assay where the incorporation of tritium labeled thymidine into Swiss 3T3 cells is measured. The assay is described as follows.

Swiss mouse 3T3 cells are maintained in Dulbecco's modified Eagle's medium (DMEM) low glucose and supplemented with 10% fetal bovine serum FBS), 2 mM 1-glutamine and 1% antibiotic-antimycotic 100 X. The cultures are incubated in 5% $CO_2$ in air at 37° C. Confluent cultures are trypsinized and plated in quadruplicate cultures for experiments. Cells are plated at $1 \times 10^5$ cells per 35 mm well in DMEM containing 10% FBS in 6-well cluster plates and are allowed to become confluent in 3 days. The cells are then made quiescent by washing them with Hank's balanced salt solution (HBSS) and incubating them for 24 hours in DMEM with 0.5% FBS. The cultures are then refed fresh DMEM containing 0.5% FBS and various concentrations of the test compounds. All compounds are dissolved in absolute ethanol, diluted with sterile filtered normal saline and added to the medium so that the final ethanol control cultures are incubated in medium containing 0.01% or less test compounds. The vehicle control cultures are incubated in medium containing 0.01% ethanol in saline. Cultures are incubated for 22 hours before pulse-labeling with [$^3$H]-thymidine ([$^3$H]-TdR).

Pulse-labeling of the cultures consists of collecting the conditioned, drug-treated or control containing media, then adding 1µ Ci/ml [$^3$H]-TdR and incubating the cultures in the [$^3$H]-TdR containing medium for 5 hours. The cells are then washed with phosphate buffered saline and fixed with 6% trichloroacetic acid (TCA). The cells are scraped from the culture wells and transferred to tubes. Each well is rinsed with 6% TCA and the rinse is added to the appropriate tubes. After centrifugation at 2800 RPM for 20 minutes at room temperature, an aliquot of the supernatant containing unincorporated [$^3$H]-TdR (S1) is transferred to scintillation tubes. Radioactivity is measured by liquid-scintillation counting using Beckman HP cocktail. The remainder S1 supernatant is decanted and 3% perchloric acid (PCA) is added to the cell pellet. The DNA is denatured by placing the tubes in heating blocks at 95° C. for 20 minutes, followed by placing the tubes in an ice bath for 15 minutes. After centrifugation as before, an aliquot of the supernatant containing [$^3$H]-TdR incorporated into DNA (S2) is assayed for radioactivity by scintillation counting.

An aliquot of the remaining S2 supernatant is assayed for quantity of DNA by the diphenylamine method. DNA standards, prepared from salmon testes DNA, and the samples are mixed with the diphenylamine reagent and incubated in a water bath with shaking at 30° C. for 6–24 hours. The diphenylamine reagent is prepared with 1.5% diphenylamine in glacial acetic acid and per 100 ml of the solution, by adding 1.5 ml of concentrated sulfuric acid and 0.5 ml of 1.6% acetaldehyde. Absorbance of the DNA standards and samples is measured in a Beckman Biomek spectrophotometer at 600 nM wavelength.

The data is expressed as CPM ([$^3$H]-TdR incorporated into DNA) per µg DNA and the mean of the quadruplicate samples is obtained for each experiment. The results are presented as per cent of the vehicle control.

General Description of Synthetic Procedures

The compounds of the invention can be made by a number of different synthetic chemical pathways. To illustrate the invention, the following detailed description is provided. The synthetic chemist will readily appreciate that the conditions set out here are specific embodiments which can be generalized to obtain any and all compounds described in the present specification.

Reaction Scheme 1

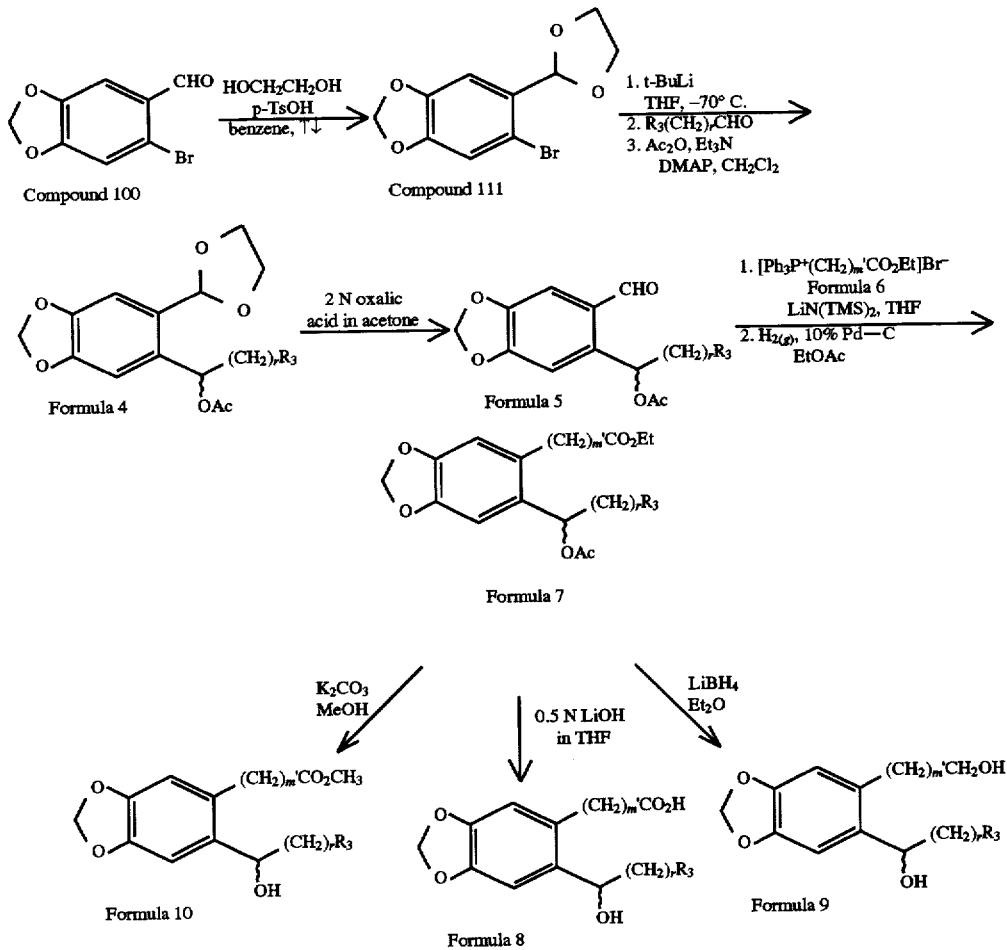

Referring now to Reaction Scheme 1, a synthetic route is disclosed for the preparation of the compounds of the invention where, with reference to Formula 1, W represents $(CH_2)_n$ and n is 1. (1,3-benzodioxole derivatives). It should be noted in connection with the synthetic schemes and processes disclosed herein that they generally follow or are analogous to the synthetic schemes and methods disclosed in U.S. Pat. No. 5,369,127, the specification of which is incorporated herein by reference in its entirety.

Referring now specifically to Reaction Scheme 1, the starting material of this scheme is 1,3-benzodioxole-6-bromo-5-carboxaldehyde (Compound 100), which can be obtained by bromination of commercially available (Aldrich) 1,3-dioxole-5-carboxaldehyde (also known as piperonal). In accordance with Reaction Scheme 1, the aldehyde function of Compound 100 is protected as an acetal by reaction with ethyleneglycol in the presence of acid. The resulting acetal (Compound 111) is reacted with an aldehyde of the formula $R_3$—$(CH_2)_r$—CHO in the presence of strong base (such as tertiary butyl lithium), and the resulting secondary alcohol is acetylated to provide a compound of Formula 4. The $R_3$ group and the symbol r of the aldehyde reagent $R_3$—$(CH_2)_r$—CHO are defined as in connection with Formula 1. For example, for the preparation of the preferred embodiments the reagent $R_3$—$(CH_2)_4$—CHO is 3-(2-thienyl)propionaldehyde and 3-(2-furyl) propionaldehyde, or such substituted derivative of 3-(2-thienyl)propionaldehyde or of 3-(2-furyl)propionaldehyde (or of any other heterocycle within the definition of Formula 1) where the substituent is $R_{11}$ as that group is defined in Formula 1. A more detailed description how to obtain the substituted heterocyclic aldehydes $R_3$—$(CH_2)_r$—CHO is provided below.

The acetal blocking group is removed, by treatment with acid, from the 5 carboxaldehyde function of the compound of Formula 4, to yield a compound of Formula 5. The compound of Formula 5 has a free aldehyde group which is reacted with a Wittig reagent of Formula 6. The symbol m' of Formula 6 is defined as an integer having the values of 1 to 7, and for this reason compounds of Formula 1 where m is between 2 to 8 can be prepared in accordance with the procedure shown in Reaction Scheme 1. Generally speaking, the Wittig reagent of Formula 6 can be prepared in accordance with synthetic procedures known in the art, for example from the brominated carboxylic acid ester, of the formula $Br(CH_2)_m$.COOEt. For example, the Wittig reagent of Formula 6 where m' is 3, can be prepared substantially in accordance with the procedure descried by Wernic at al. in *J. Org. Chem.*, 1989, 54, 4224–4228 at page 4226. The olephinic product of the Wittig reaction between compounds of Formula 5 and Formula 6 is thereafter hydrogenated to yield a compound of Formula 7. As it will be recognized by those skilled in the art, Formula 7 depicts compounds of Formula 1, where the $R_2$ group is acetyl ($COCH_3$) and $R_1$ is ethyl carboxylate (CO$_2$Et). The compounds of Formula 7 can be converted to further compounds within the scope of Formula 1, such as into the compounds of Formula 8 where R$_2$ is H and R$_1$ is CO$_2$H, obtainable by saponification; into compounds of Formula 9 where R$_2$ is H and R$_1$ is CH2OH, obtainable by reduction with lithium borohydride, and into compounds of Formula 10 where R$_2$ is H and R$_1$ is methyl (or other alkyl), obtainable by saponification and transesterification.

It will be readily apparent to those skilled in the art that the selection of a suitable synthetic route between Reaction Scheme 1 and Reaction Scheme 2 will be influenced by several factors, including the nature of the R$_{11}$ substituent(s) present in the heterocyclic ring of the R$_3$ group. A person having ordinary skill in the art of synthetic organic chemistry is readily able to modify or adjust the conditions of the herein disclosed synthetic schemes so as to retain or form a particular R$_{11}$ substituent throughout the series of reactions

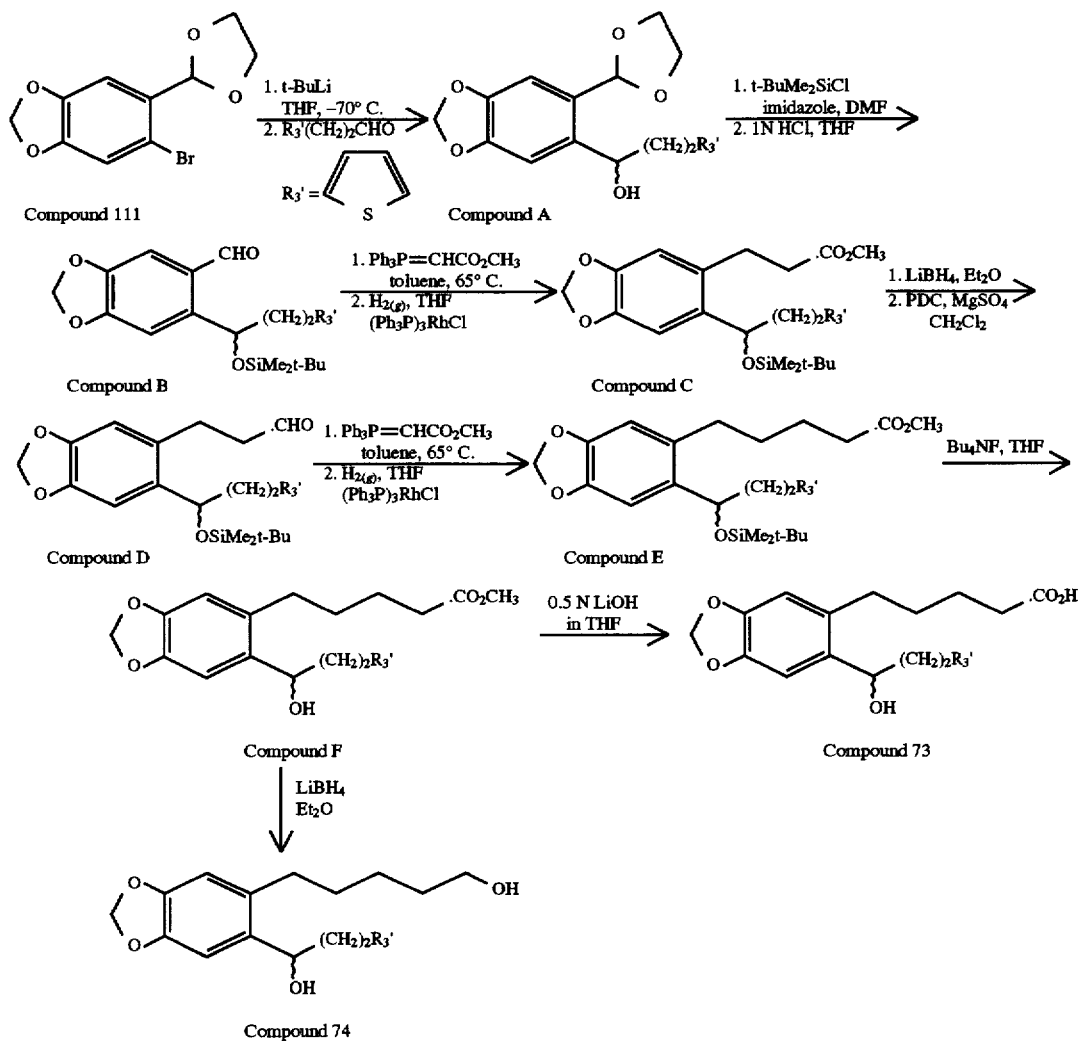

Reaction Scheme 2 shows an alternative synthetic route to the compounds of the invention, specifically illustrated for compounds where the R$_3$ group is 2-thienyl. It should be understood however that, generally speaking, this synthetic route is suitable for the synthesis of many compounds of Formula 1, where w is (CH$_2$)$_n$ and n is 1. The synthetic route of Reaction Scheme 2 differs from the synthetic route shown in Reaction Scheme 1 in that the side chain designated (CH$_2$)$_m$R$_1$ in Formula 1 is built from the corresponding aldehyde through not one but two Wittig reactions. In the example illustrated in Reaction Scheme 2 a "two carbon fragment" is added in each Wittig reaction, eventually leading to a straight side chain of 5 carbons. The specific chemical reactions depicted in Reaction Scheme 2 are described in the Specific Examples below.

leading to compounds of Formula 1. On occasion this may require the use of blocking or protecting groups of the type well known in the art, or changes in reagents or reaction conditions from those specifically described for the present examples.

Referring back now to Reaction Scheme 1, generally speaking, the ester functionality of the compounds of Formula 7 can be converted to the amide, sulfonamide, aldehyde, ketone, acetal, ketal, and amino functionalities set forth in connection with Formula 1 by reactions which are per se well known to the practicing organic chemist, are described in standard handbooks and textbooks of organic chemistry, and therefore do not need to be described here. The compounds of Formula 1 where m=1, cannot be made directly by the Wittig reaction outlined in Reaction Scheme 1. However, these compounds can be obtained by reaction of the aldehyde of Formula 5 with a Grignard or like reagent, followed by such synthetic steps to build the —$CH_2$—$R_1$ side chain on the 1,3-benzodioxole nucleus, which will be apparent to those skilled in the art in light of the present disclosure.

olefinic compound is hydrogenated and the t-butyldiphenylsilyl blocking group is removed for example by treatment with tetrabutylammonium fluoride in tetrahydrofuran, to yield compounds of Formula 12. As is readily apparent, compounds of Formula 12 are such compounds of Formula 1 where the $R_1$ group is $CO_2Et$, and the $R_2$ group is H. These compounds can be reduced to the Reaction Scheme 3

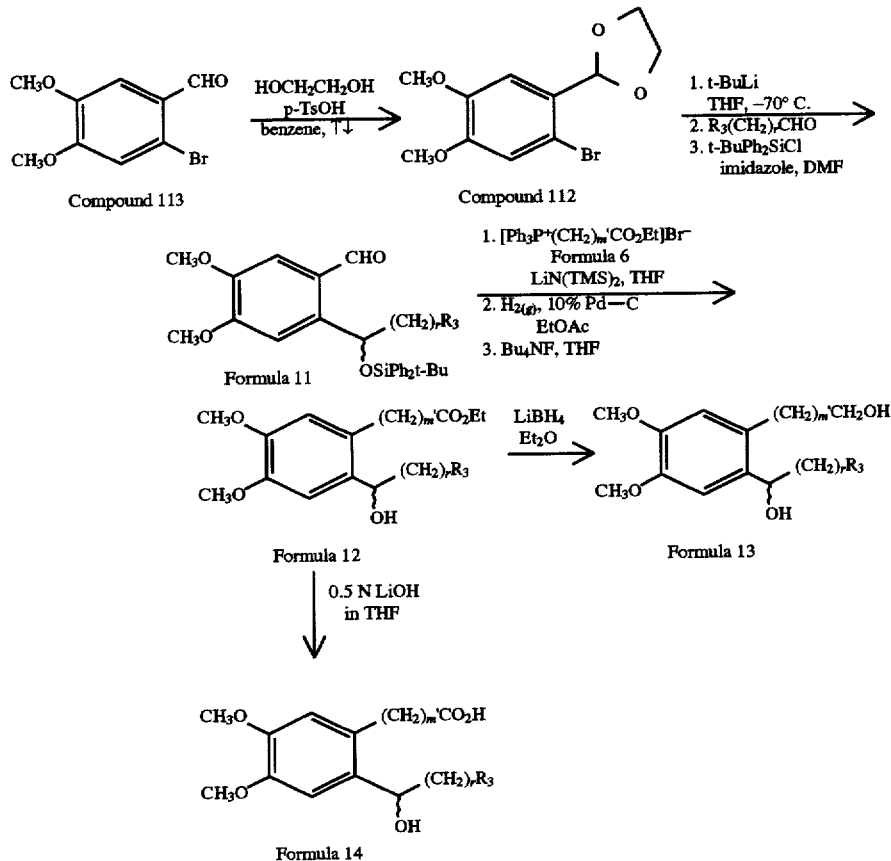

Referring now to Reaction Scheme 3, synthesis of the compounds of the invention is disclosed where in accordance with Formula 1 the symbol W represents two alkyl, specifically methyl groups, attached to the oxygens of the benzene nucleus. The starting material for this synthetic scheme is commercially available (Aldrich) 2-bromo-4,5-dimethoxybenzaldehyde, also known as 6-bromo veratraldehyde, (Compound 113). In accordance with Reaction Scheme 3, the aldehyde group of Compound 113 is protected by reaction with ethylene glycol to obtain the acetal (1,3-dioxolane) derivative (Compound 112). Compound 112 is reacted with an aldehyde of the formula $R_3$—$(CH_2)_r$—CHO in the presence of strong base such as tertiary butyl lithium. The secondary hydroxyl group which is obtained as a result of reaction with the aldehyde is protected by a suitable base-stable protective group, such as the tertiary-butyldiphenylsilyl group, to yield the compound of Formula 11. During the reaction of the secondary alcohol with t-butyldiphenylsilyl chloride in the presence of mild acid (imidazole) in dimethylformamide as a solvent, the acetal blocking group of the benxaldehyde function is also removed. In the next step the compound of Formula 11 is reacted with the Wittig reagent of Formula 6. The resulting primary alcohol ($R_1$ of Formula 1 is $CH_2OH$ as in Formula 13) or can be saponified to yield the free carboxylic acid (as in Formula 14), as described above for the analogous reactions in Reaction Scheme 1. The ethylcarboxylate function of the compounds of Formula 12 can also be converted into the amide, sulfonamide, amine and other functionalities set forth in connection with Formula 1, by reactions well known in the art, as explained above in connection with Reaction Scheme 1.

Generally speaking the reagents of the formula $R_3$—$(CH_2)_r$—CHO are prepared in accordance with state-of-the-am The specific reagent of this formula, which is used in Reaction Scheme 2 is 3-(2-thienyl)propionaldehyde. The analogous furan and pyridine derivatives of the invention can be made substantially in accordance with Reaction Scheme 2, by using 3-(2-furyl)propionaldehyde, 3-(2-pyridyl)propionaldehyde and 3-(3-pyridyl)propionaldehyde, respectively. The aldehyde reagents of the formula $R_3$—$(CH_2)_r$—CHO where the heterocyclic portion bears one or more $R_{11}$ substituent (other than hydrogen) are also available substantially in accordance with the state of the art. Examples of reagents, which are suitable for the synthesis of several preferred compounds of the invention (see Table 1)

are as follows: 3-(5-methyl-2-furyl)propionaldehyde, 3-(5-bromo-2-furyl)propionaldehyde, 3-(5-trifluoromethyl-2-furyl)propionaldehyde, 3-(5-methyl-2-thienyl) propionaldehyde, 3-(5-bromo-2-thienyl)propionaldehyde, 3-(5-trifluoromethyl-2-thienyl)propionaldehyde, 3-(2-methyl-4-furyl)propionaldehyde, 3-(2-bromo-4-furyl) propionaldehyde, 3-(2-trifluoromethyl-4-furyl) propionaldehyde, 3-(2-methyl-4-thienyl)propionaldehyde, 3-(2-bromo-4-thienyl)propionaldehyde, 3-(2-trifluoromethyl-4-thienyl)propionaldehyde. Still further, examples of the aldehyde reagents for the synthesis of pyridine derivatives of Formula 1 are: 3-(5-methyl-2-pyridyl)propionaldehyde, 3-(5-bromo-2-pyridyl) propionaldehyde, 3-(5-trifluoromethyl-2-pyridylyl) propionaldehyde, 3-(2-methyl-4-pyridyl)propionaldehyde, 3-(2-bromo-4-pyridyl)propionaldehyde, 3-(2-trifluoromethyl-4-pyridylyl)propionaldehyde, 3-(6-methyl-2-pyridyl)propionaldehyde, 3-(6-bromo-2-pyridyl) propionaldehyde, 3-(6-trifluoromethyl-2-pyridylyl) propionaldehyde.

$_3$RhCl) to provide the saturated carboxylate esters of Formula 18. The carboxylate ester function of the compounds of Formula 18 is converted to an aldehyde by reduction with lithium borohydride, followed by oxidation with pyridinium dichromate to yield the propionaldehyde derivatives of Formula 19.

Compounds of Formula 15 or of Formula 16, if not available by commercially, can be made in accordance with the chemical literature, and specifically in accordance with or in analogy to the methodology described in the publication G. C. M. Lee et al. *J. Org. Chem.* 1992, 57, 3126–3131, which is expressly incorporated herein by reference. Reaction Scheme 5 summarizes this methodology to obtain 5-substituted 3-formyl-furan or thiophene compounds. The synthesis of 3 or 5 substituted 2-formyl-furans or thiophenes is already illustrated by the first reaction in Reaction Scheme 4.

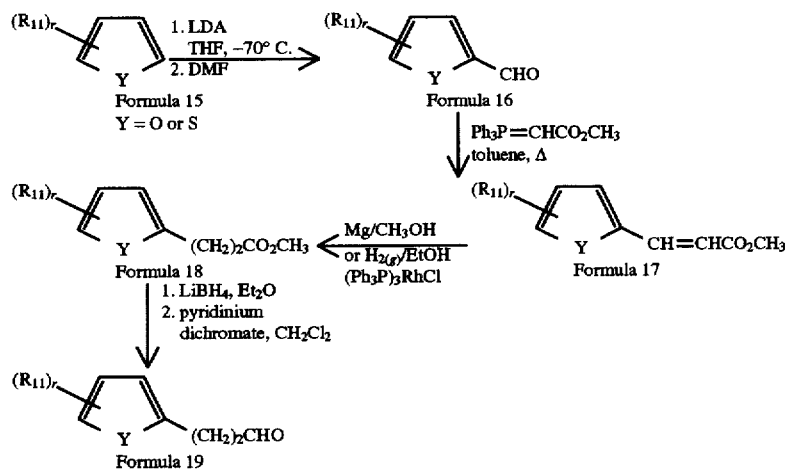

Reaction Scheme 4 illustrates the synthesis of 3-(2-thienyl)-propionaldehyde derivatives and of 3-(2-furyl) propionaldehyde derivatives which are within the scope of the formula R$_3$—(CH$_2$)$_2$—CHO where the heterocyclic portion bears one or more R$_{11}$ substituents. Examples for these compounds were described immediately above. In this reaction scheme the symbol Y represents O or S, indicating that the reaction sequence is applied here for the synthesis of thiophene and furan derivatives. However, as it will be readily apparent to those skilled in the art, the steps described in Reaction Scheme 4 can also be applied, with such modifications which will be apparent to those skilled in the art, for the synthesis of other heterocyclic substituted propionaldehydes and homologs.

Thus a furan or thiophene derivative (Formula 15) which already has the R$_{11}$ substituent(s) is reacted with lithiumdiethylamide (LDA) followed by dimethylformamide (DMF) to introduce a formyl group into the thiophene or furan nucleus and provide compounds of Formula 16. The compounds of Formula 16 are reacted with methyl (triphenylphosphoranylidene)acetate (available from Aldrich) in a Wittig reaction to yield compounds of Formula 17. The olefinic bond of the compounds of Formula 17 is saturated by treatment with magnesium in methanol, or by hydrogenation in the presence of Wilkinson catalyst ((Ph$_3$P)

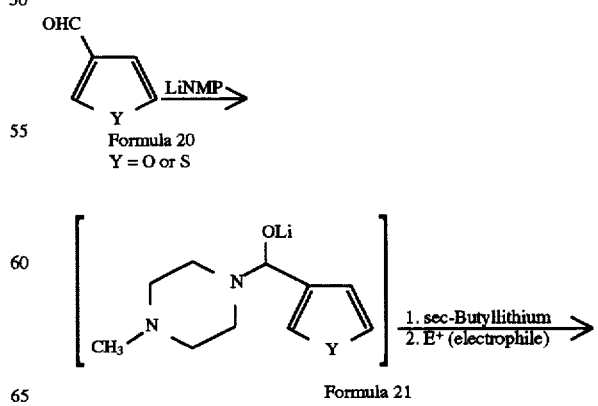

-continued
Reaction Scheme 5

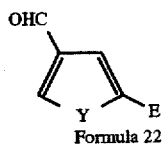

Formula 22

Thus, as shown in Reaction Scheme 5 furan-3-aldehyde or thiophen-3-aldehyde of Formula 20 is reacted with lithium N-methylpiprazine (LiNMP). It is believed as a matter of reaction mechanism and theory that this reaction results in the formation of an intermediate of Formula 21 wherein the 2- position of the 5 membered ring is sterically blocked. Secondary butyllithium and an electrophile such a bromine, chlorine, methyliodide etc. is introduced into the reaction mixture, resulting in introduction of the electrophile into the 5-position of the 5 membered ring, as shown in Formula 22.

SPECIFIC EXAMPLES

1,3-Benzodioxole-6-bromo-5-carboxaldehyde (Compound 100)

To a solution of 1,3-benzodioxole-5-carboxaldehyde (piperonal, Aldrich, 30 g., 0.20 mol) in glacial acetic acid (60 ml) was added a solution of bromine (12.0 mL, 0.23 mol) in HOAc (37.5 mL). The resultant solution was stirred for 16 hours and poured into $H_2O$ (1500 mL). The precipitate was removed by vacuum filtration and washed with 0.2N aqueous sodium thiosulfate followed by ice-cold $Et_2O$. The white solid was dissolved in MeOH with heating and upon allowing to cool to 23° C. white needles crystallized. The crystals were collected by vacuum filtration to give 22.4 g (49%) of the title compound.

2-Bromo-4,5-methylenedioxy-5-1,3-dioxolanylbenzene (Compound 111)

A solution of 1,3-benzodioxole-6-bromo-5-carboxaldehyde (Compound 100, 2.0 g, 8.77 mmol), ethylene glycol (2.4 ml., 43.8 mmol) and p-toluene sulfonic acid (83 mg, 0.438 mmol) in benzene (43 mL) was heated to reflux for 16 hours with azeotropical removal of water. The solvent was removed in vacuo and the residue was diluted with EtOAc. After washing with $H_2O$ (2×) and saturated aqueous $NaHCO_3$ the organic portion was dried ($MgSO_4$), filtered and concentrated in vacuo to give 2.28 g (96%) of the title compound acetal (dioxolane) derivative. $^1$H NMR (300 MHz, $CDCl_3$) δ 7.08 (s, 1H), 7.00 (s, 1H), 6.02 (s, 1H), 5.90 (s, 2H), 4.18–4.03 (m, 4H).

1-Bromo-2-(1,3-dioxolanyl)-4,5-dimethoxybenzene (Compound 112)

Following substantially the procedure described for the preparation of 2-bromo-4,5-methylenedioxy-1-1,3-dioxolanylbenzene (Compound 111), the title compound was obtained in 97% yield from commercially available (Aldrich) 2-bromo-4,5-dimethoxybenzaldehyde (Compound 113, 5.0 g, 0.02 mmol) by reaction with ethylene glycol (6.33 g, 0.102 mol) in tolune (80 ml) in the presence of p-toluenesulfonic acid (190 mg, 0.001 mol).

$^1$H NMR (300 MHz, $CDCl_3$) δ 7.12 (s, 1H), 7.02 (s, 1H), 6.00 (s, 1H), 4.21- 4.07 (m, 4H), 3.90 (s, 3H), 3.89 (s, 3H).

(±)-5-(1,3-Dioxolanyl)-[6-(1-hydroxy-3-(2-thienyl) propyl)]-1,3-benzo dioxole. (Compound A)

A solution of 2-bromo-4,5-methylenedioxy-5-1,3-dioxolanylbenzene (Compound 111, 1.37g, 5.02 mmol) in THF 20 mL) was cooled to −78° C. and t-BuLi (6.0 mL of a 1.7M solution in pentane, 10.30 mmol) was added dropwise. After 0.5 hours 3-(2-thienyl)propionaldehyde 469 mg, 3.35 mmol) in THF (8.0 mL) was added, the reaction was stirred at −78° C. for 0.5 hours, warmed to 23° C. and quenched with saturated aqueous $NH_4Cl$. The aqueous layer was separated and extracted with EtOAc. The combined organic portions were dried ($MgSO_4$), filtered and concentrated in vacuo. Flash column chromatography (silica gel, 3:1 hex/EtOAc) gave the racemic title compound (0.772 g) in 69% yield. $^1$H NMR (300 MHz, $CDCl_3$) δ 7.13 (d, J=5.1 Hz, 1H), 7.05 (s, 2H), 6.93 (dd, J=3.6, 5.1 Hz, 1H), 5.83 (d, J=3.6 Hz, 1H), 5.97 (s, 2H), 5.83 (s, 1H), 5.00–5.03 (m, 1H), 3.95–4.12 (m, 4H), 2.92–3.10 (m, 2H), 2.41 (d, J=1.8 Hz, 1H), 2.06–2.23 (m, 2H).

(±)-5-[[6-(1-t-butyldimethylsilyloxy-3-(2-thienyl) propyl]-1,3-benzodioxolyl]carboxaldehyde (Compound B)

A solution of (±)-5-(1,3-dioxolanyl)-[6-(1-hydroxy-3-(2-thienyl)propyl)]-1,3-benzodioxole (Compound A, 770 mg, 2.30 mmol), imidazole (314 mg, 4.61 mmol) and t-butyldimethysilyl chloride (521 mg, 3.46 mmol) in DMF (4.6 mL) was stirred at 23° C. for 16 hours. The reaction mixture was diluted with $Et_2O$ and washed with 1N HCl, saturated aqueous $NaHCO_3$ and brine. The organic portion was dried ($MgSO_4$), filtered and the filtrate concentrated in vacuo to give 562 mg (55%) of the crude silyl ether as an oil.

The residue was diluted with a 1:1 mixture of 1N HCl:THF (12.0 mL) and stirred for 1 hour at 23° C. The reaction mixture was extracted with EtOAc (2×) and the combined organics were washed with saturated aqueous $NaHCO_3$, brine, dried ($MgSO_4$), filtered and concentrated in vacuo. Flash column chromatography (silica gel, 9:1 hex/EtOAc) gave a 99% yield of the title compound. $^1$H NMR (300 MHz, $CDCl_3$) δ 10.13 (s, 1H), 7.28 (s, 1H), 7.16 (s, 1H), 7.11 (d, J=5.4 Hz, 1H)D, 6.90 (dd, J=3.6, 5.4 Hz, 1H), 6.78 (d, J=3.6 Hz, 1H), 6.07 (d, J=5.1 Hz, 2H), 5.54–5.56 (m, 1H), 2.94 (t, J=8.4 Hz, 2H), 2.04–2.07 (m, 2H), 0.91 (s, 9H), 0.07 (s, 3H),-0.13 (s, 3H).

(±)-Methyl-3-[[6-(1-t-butyldimethylsilyloxy-3-(2-thienyl)propyl)]-1,3-benzodioxolyl]propanoate (Compound C)

A mixture of (±)-5-[[6-t-butyldimethylsilyloxy-3-(2-thienyl)-propyl)]-1,3-benzodioxolyl] carboxaldehyde (Compound B, 671 mg, 1.66 mmol) and methyl (triphenylphosphoranylidene)acetate (2.22 g, 6.64 mmol) in toluene was stirred at 23° C. for 96 hours. The reaction mixture was concentrated in vacuo. The residue was diluted with $Et_2O$, filtered under vacuum and the filtrate was concentrated in vacuo. Purification by flushing through a plug of silica gel (19:1 hex/EtOAc) gave 730 mg (99%) of intermediary ene-ester as an oil.

The oil obtained above, Wilkinson's catalyst (700 mg) and THF (9.0 mL) were thoroughly degassed and purged under an atmosphere of hydrogen gas. After 16 hours the reaction mixture was concentrated in vacuo and the residue was purified by flash column chromatography (silica gel, 19:1 hex/EtOAc) to give 666.3 mg (87%) of the title compound. $^1$H NMR (300 MHz, $CDCl_3$) δ 7.10 (d, J=5.4 Hz, 1H), 6.99 (s, 1H), 6.91 (dd, J=3.6, 5.4 Hz, 1H), 6.78 (d, J=3.6 Hz, 1H), 6.58 (s, 1H), 5.92 (d, J=6.3 Hz, 2H), 4.88–4.92 (m, 1H), 3.67 (s, 3H), 2.78–2.96 (m, 4H), 2.50 (t, J=7.8 Hz, 2H), 1.85–2.04 (m, 2H), 0.91 (s, 9H), 0.05 (s, 3H),-0.17 (s, 3H).

(±)-3-[[6-(1-t-butyldimethylsilyloxy-3-(2-thienyl) propyl)]-1,3-benzodioxolyl]propionaldehyde (Compound D)

Lithium borohydride (32.6 mg, 1.49 mmol) was added to a solution of the (±)-methyl-3-[[6-(1-t- butyldimethylsilyloxy-3-(2-thienyl)propyl)]-1,3-benzodioxololyl]propanoate (Compound C, 666 mg, 1.44 mmol) in Et₂O (4.5 mL). After 12 hours the reaction was quenched with 1N NaOH, stirred 1 hour, and then extracted with EtOAc. The organic portion was dried (MgSO₄), filtered and concentrated in vacuo to give a viscous oil.

The crude alcohol obtained above was diluted with CH₂Cl₂ (7.5 mL) then MgSO₄ (840 mg), crushed 4 A sieves (840 mg) and pyridinium dichromate (840 mg, 2.23 mmol) were added. After 16 hours the reaction mixture was diluted with Et₂O and filtered through celite. The filtrate was concentrated in vacuo and the residue was purified by flash column chromatography (silica gel, 9:1 hex/EtOAc) to afford 317 mg (51%) of the title compound. ¹H NMR (300 MHz, CDCl₃) δ 9.60 (s, 1H), 7.11 (d, J=5.1 Hz, 1H), 6.99 (s, 1H), 6.93 (dd, J=3.3, 5.1 Hz, 1H), 6.79 (d, J=3.3 Hz, 1 1H), 6.59 (s, 1H), 5.93 (d, J=6.4 Hz, 2H), 4.88–4.92 (m, 1H), 2.76–2.97 (m, 4H), 2.52 (t, J=7.6 Hz, 2H), 1.84–2.06 (m, 2H), 0.91 (s, 9H), 0.05 (s, 3H)-0.18 (s, 3H).

(±)-Methyl-5-[[6-(1-t-butyldimethylsilyloxy-3-(2-thienyl)propyl)]-1,3-benzodioxolyl]pentanoate (Compound E)

By a procedure similar to that described for Compound C above, the title compound was prepared by condensation of (±)-3-[[6-(1-t-butyldimethylsilyloxy-3-(2-thienyl)propyl)]-1,3-benzodioxolyl] propionaldehyde (Compound D, 317 mg, 0.733 mmol) with methyl(triphenylphosphoranylidene) acetate (382 mg, 1.14 mmol) in toluene (3.0 mL) followed by hydrogenation with Wilkinson's catalyst (350 mg) in THF (3.0 mL) in 50% overall yield. ¹H NMR (300 MHz, CDCl₃) δ 7.12 (d, J=5.1 Hz, 1H), 6.99 (s, 1H), 6.92 (dd, J=4.5, 5.1 Hz, 1H), 6.80 (d, J=4.4 Hz, 1H), 6.57 (s, 1H), 5.91 (dd, J=1.5, 9.9 Hz, 2H), 4.85–4.89 (m, 1H), 3.68 (s, 3H), 2.96 (t, J=8.1 Hz, 2H), 2.42–2.49 (m, 2H), 2.31 (t, J=6.9 Hz, 2H), 1.78–2.06 (m, 2H), 1.48–1.67 (m, 4H), 0.92 (s, 9H), 0.05 (s, 3H), -0.18 (s, 3H).

(±)-Methyl-5-[[6-(1-hydroxy-3-(2-thienyl)propyl)]-1,3-benzodioxolyl]pentanoate (Compound 73)

Tetrabutylammonium fluoride (0.58 mL of a 1.0M solution in THF, 0.58 mmol) was added to (±)-methyl-5-[[6-(1-t-butyldimethylilyloxy-3-(2-thienyl)propyl)]-1,3-benzodioxolyl]pentanoate (Compound E, 178 mg, 0.36 mmol) in THF (4.5 mL). After 16 hours the reaction was diluted with EtOAc and washed with H₂O. The organic portion was dried (MgSO₄) filtered and concentrated in vacuo. Flash column chromatography (silica gel, 2:1 hex/EtOAc) gave 135 mg (99%) of the title compound. ¹H NMR (300 MHz, CDCl₃) δ 7.14 (d, J=5.1 Hz, 1H), 7.01 (s, 1H), 6.93 (dd, J=3.3, 5.1 Hz, 1H), 6.83 (d, J =3.3 Hz, 1H), 6.60 (s, 1H), 5.92 (s, 2H), 4.88–4.91 (m, 1H), 3.67 (s, 3H), 2.96–3.03 (m, 2H), 2.43–2.49 (m, 2H), 2.29 (t, J=6.9 Hz, 2H), 1.88–2.20 (m, 2H), 1.80 (d, J=3.0 Hz, 1H), 1.44–1.66 (m, 4H).

(±)-5-[[6-(1-hydroxy-3-(2-thienyl)propyl]-1,3-benzodioxolyl]pentanol (Compound 74)

Lithium borohydride (2.1 mg, 0.096 mmol) was added to a solution of (±)-methyl-5-[[6-(1-hydroxy-3-(2-thienyl)propyl]-1,3-benzodioxolyl]pentanoate (Compound 73, 36.0 mg, 0.096 mmol) in Et₂O (2.0 mL) at 23° C. After 12 hours the reaction was quenched with 1N NaOH, stirred 1 hour, and extracted with EtOAc. The organic portion was dried (MgSO₄), filtered and concentrated in vacuo. Purification by flash column chromatography (silica gel, 2:1 hex/EtOAc)

provided 32.6 mg (98%) of the title compound. ¹H NMR (300 MHz, CDCl₃) δ 7.14 (d, J=5.5 Hz, 1H), 7.01 (s, 1H), 6.93 (dd, J=3.3, 5.5 Hz, 1H), 6.84 (d, J=3.3 Hz, 1H), 6.61 (s, 1H), 5.92 (s, 2H), 4.88–4.92 (m, 1H), 3.63 (t, J=5.7 Hz, 2H), 2.97–3.03 (m, 2H), 2.43–2.49 (m, 2H), 1.84–2.20 (m, 3H), 1.26–1.59 (m, 7H).

(±)-5-[[6-(1-hydroxy-3-(2-thienyl)propyl)]-1,3-benzodioxolyl]pentanoic acid (Compound 75)

A mixture of (±)-methyl-5-[[6-(1-hydroxy-3-(2-thienyl)propyl-1,3-benzodioxolyl]pentanoate (Compound 73, 35 mg, 0.093 mmol) and lithium hydroxide (0.37 ml of a 0.5N solution in H₂O, 0.186 mmol) in THF (0.74 mL) was stirred at 23° C. for 16 hours. The mixture was acidified with 1N HCl and extracted with EtOAc. The organic portion was dried (MgSO₄) filtered and concentrated in vacuo. Flash column chromatography (silica gel, 100% EtOAc) afforded 33.3 mg (99%) of the title compound. ¹H NMR (300 MHz, CDCl₃) δ 12.0 (brs, 1H), 7.14 (d, J=5.1 Hz, 1H), 7.00 (s, 1H), 6.93 (dd, J=3.3, 5.1 Hz, 1H), 6.83 (d, J=3.3 Hz, 1H), 6.59 (s, 1H), 5.91 (s, 2H), 4.87–4.92 (m, 1H), 2.97 (t, J=5.4 Hz, 2H), 2.43–2.47 (m, 2H), 2.32 (t, J=6.9 Hz, 2H), 1.86–2.18 (m, 2H), 1.44–1.64 (m, 5H).

What is claimed is:

1. A compound of the formula

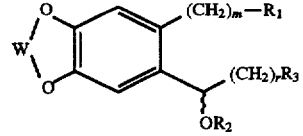

where

W is (CH₂)ₙ. where n is 1 or 2;

m is an integer between 1 and 8;

R₁ is COOH or a pharmaceutically acceptable salt thereof, COOR₄, CONR₅R₆, CONR₅SO₂R₇,CH₂OH, CH₂OR₇, CH₂O—COR₇, CH₂O—CONR₅R₇, CH₂OCOOR₇, CH₂NR₅R₆, CH₂NR₅COR₇, CHO, CH(OR₈)₂, CH(OR₉O), —COR₁₀, CR₁₀(OR₈)₂, or CR₁₀(OR₉O), where R₄ is an alkyl group of 1 to 10 carbons, or a cycloalkyl group of 5 to 10 carbons, or R₄ is phenyl or lower alkylphenyl, R₅ and R₆ independently are hydrogen, an alkyl group of 1 to 10 carbons, or a cycloalkyl group of 5 to 10 carbons, or phenyl or lower alkylphenyl, R₇ is alkyl of 1 to 10 carbons, phenyl or lower alkylphenyl, R₈ is lower alkyl, and R₉ is divalent alkyl radical of 2–5 carbons. R₁₀ is an alkyl or cycloalkyl containing 1 to 5 carbons;

R₂ is H, COR₇, R₇, CO—OR₇, CO—NR₂R₇, PO(OH)OR₇, PO(OR₇)₂, POR₇OH, or POR₇(OR₇);

R₃ is HETEROCYCLIC—(R₁₁)ₚ, where HETEROCYCLIC is a 5 or six-membered heterocyclic ring containing 1 or 2 heteroatoms selected from N, S, and O;

R₁₁ is independently lower alkyl of 1–6 carbons, halogen, fluoro-substituted lower alkyl of 1–6 carbons, C≡N, NO₂, SO₂R₁₂, COOH, COOR₁₂, CONH₂, CONHR₁₂, CON(R₁₂)₂, or CO—R₁₂;

p is an integer between 1–3, r is an integer between 1–5, and

R₁₂ is lower alkyl of 1–6 carbons.

2. A compound of claim 1 wherein W represents (CH₂)ₙ and n is 1.

3. A compound of claim 1 wherein W represents lower alkyl groups attached to each oxygen.

4. A compound of claim 1 wherein m is 4.

5. A compound of claim 1 wherein $R_1$ is COOH, COOR$_4$ or CH$_2$OH.

6. A compound of claim 1 wherein r is 2.

7. A compound of claim 1 wherein $R_3$ is HETEROCYCLIC—(R$_{11}$)$_p$, where HETEROCYCLIC is a divalent radical of thiophene, furan, thiazole or oxazole.

8. A compound of claim 1 where p is 1, and $R_{11}$ is CH$_3$, halogen or trifluoromethyl.

9. A compound of claim 1 wherein $R_2$ is H or COR$_7$ wherein R$_7$ is lower alkyl.

10. A compound of the formula

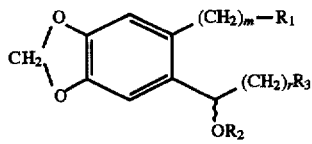

wherein
m is an integer between 1 and 8;
$R_1$ is COOH or a pharmaceutically acceptable salt thereof, COOR$_4$, CONR$_5$R$_6$, CONR$_5$SO$_2$R$_7$, CH$_2$OH, CH$_2$OR$_7$, CH$_2$O—COR$_7$, CH$_2$O—CONR$_5$R$_7$, CH$_2$OCOOR$_7$, CH$_2$NH$_2$, CH$_2$NR$_5$R$_6$, CH$_2$NR$_5$COR$_7$, where R$_4$ is an alkyl group of 1 to 10 carbons, or a cycloalkyl group of 5 to 10 carbons, or R$_4$ is phenyl or lower alkylphenyl, R$_5$ and R$_6$ independently are hydrogen, an alkyl group of 1 to 10 carbons, or a cycloalkyl group of 5 to 10 carbons, or phenyl or lower alkylphenyl, R$_7$ is alkyl of 1 to 10 carbons, phenyl or lower alkylphenyl;

$R_2$ is H, COR$_7$, R$_7$, CO—OR$_7$, CO—NR$_5$R$_7$, PO(OH)OR$_7$, PO(OR$_7$)$_2$, POR$_7$OH, or POR$_7$(OR$_7$);

$R_3$ is HETEROCYCLIC-(R$_{11}$)$_p$, where HETEROCYCLIC is selected from furan and thiophene;

$R_{11}$ is independently lower alkyl of 1–6 carbons, halogen, fluoro-substituted lower alkyl of 1–6 carbons, C≡N, NO$_2$, SO$_2$R$_{12}$, COOH, COOR$_{12}$, CONH$_2$, CONHR$_{12}$, CON(R$_{12}$)$_2$, or CO—R$_{12}$;

p is an integer between 1–3,
r is an integer between 1–5, and
$R_{12}$ is lower alkyl of 1–6 carbons.

11. A compound of claim 10 wherein r is 2.

12. A compound of claim 11 wherein m is 4.

13. A compound of claim 12 wherein $R_1$ is CO$_2$CH$_3$, CO$_2$H or CH$_2$OH.

14. A compound of claim 13 wherein p is 1.

15. A compound of claim 14 wherein $R_{11}$ is selected from CH$_3$, halogen and CF$_3$.

* * * * *

UNITED STATES PATENT AND TRADEMARK OFFICE
CERTIFICATE OF CORRECTION

PATENT NO.   : 5,710,288
DATED        : January 20, 1998
INVENTOR(S)  : Burk et al.

It is certified that error appears in the above-indentified patent and that said Letters Patent is hereby corrected as shown below:

Column 3, line 3, "cycloallcyl" should be --cycloalkyl--.

Column 3, line 28, "GENERAL EMBODIMENTS" should be a separate heading.

Column 3, line 31, "theft" should be --their--.

Column 5, line 54, after "4", in the next column, add --2--.

Column 6, line 22, after "$CF_3$" in the next column delete "2" and add --4--.

Column 9, line 65, "$R_3-(CH_2)_4-CHO$" should be --$R_3-(CH_2)_r-CHO$--.

Column 10, line 59, "$Br(CH_2)_m$,COOEt" should be --$Br(CH_2)_m$,COOEt--.

Column 10, line 61, "descried" should be --described--.

Column 11, line 5, "CH2OH" should be --$CH_2OH$--.

Column 14, line 56, "am" should be --art.--

Column 18, line 35, after "7.11 (d, J=5.4 Hz, 1H)", delete "D".

Column 19, line 2, "benzodioxololyl" should be --benzodioxolyl--.

Column 19, line 16, after "6.79 (d, J=3.3 Hz,", delete the first occurrence of "1".

Column 19, line 22, "-1.3-" should be -- -1,3- --.

Column 20, line 51, "$CO-NR_2R_7$" should be --$CO-NR_5R_7$--.

Column 21, line 11, "R," should be --$R_7$--.

UNITED STATES PATENT AND TRADEMARK OFFICE
CERTIFICATE OF CORRECTION

PATENT NO. : 5,710,288
DATED     : January 20, 1998
INVENTOR(S) : Burk et al.

It is certified that error appears in the above-identified patent and that said Letters Patent is hereby corrected as shown below:

```
Column  2, line  7, "Prostaglandisn" should be --Prostaglandins--.
Column  4, line  4, "tromethanine" should be --tromethamine--.
Column 13, line 65, "benxaldehyde" should be --benzaldehyde--.
Column 15, line 14, "pyridylyl" should be --pyridyl--.
Column 15, line 17, "pyridylyl" should be --pyridyl--.
Column 15, line 19, "pyridylyl" should be --pyridyl--.
Column 16, line 10, after "available", delete "by".
Column 17, line 59, "tolune" should be --toluene--.
Column 18, line  1, after "THF", add --(--.
Column 18, line  3, after "propionaldehyde", add --(--.
Column 18, line 22, "t-butyldimethsilyl" should be
          --t-butyldimethylsilyl--.
Column 19, line 44, "t-butyldimethylilyloxy" should be
          --t-butyldimethylsilyloxy--.
```

Signed and Sealed this

Twenty-third Day of June, 1998

Attest:

BRUCE LEHMAN

Attesting Officer

Commissioner of Patents and Trademarks

UNITED STATES PATENT AND TRADEMARK OFFICE
CERTIFICATE OF CORRRECTION

PATENT NO. : 5,710,288
DATED : January 20, 1998
INVENTOR(S) : Burk, et al It is certified that error appears in the above-identified patent and that said Letters Patent is hereby corrected as shown below:

On the title page, under item [56], insert the following:

U. S. PATENT DOCUMENTS

| EXAMINER INITIAL | | PATENT NUMBER | | | | | | | ISSUE DATE | PATENTEE | CLASS | SUBCLASS | FILING DATE IF APPROPRIATE |
|---|---|---|---|---|---|---|---|---|---|---|---|---|---|
| | | 5 | 0 | 6 | 6 | 6 | 4 | 4 | 11/19/91 | Poli et al. | | | |
| | | 5 | 0 | 9 | 1 | 5 | 2 | 8 | 2/25/92 | Gluchowski | | | |
| | | 5 | 1 | 5 | 1 | 4 | 4 | 0 | 9/29/92 | Gluchowski | | | |
| | | 5 | 3 | 6 | 9 | 1 | 2 | 7 | 11/29/94 | Burk et al. | | | |
| | | | | | | | | | | | | | |

Signed and Sealed this

Ninth Day of March, 1999

*Attest:*

*Attesting Officer*

Q. TODD DICKINSON

*Acting Commissioner of Patents and Trademarks*